United States Patent [19]
Coates et al.

[11] Patent Number: 5,230,830
[45] Date of Patent: Jul. 27, 1993

[54] CYANOHYDRIN DERIVATIVES AND THEIR USE IN LIQUID CRYSTAL MATERIALS AND DEVICES

[75] Inventors: David Coates, Wimborne; Simon Greenfield, Poole; Ian C. Sage, Broadstone, all of England

[73] Assignee: The Secrteary of State for Defence in Her Britannic Majesty's Government of the United Kingdom of Great Britain and Northern Ireland, London, England

[21] Appl. No.: 868,687

[22] Filed: Apr. 15, 1992

Related U.S. Application Data

[62] Division of Ser. No. 543,744, Jul. 11, 1990, Pat. No. 5,133,896.

[30] Foreign Application Priority Data

Dec. 18, 1987 [GB] United Kingdom ............... 8729502

[51] Int. Cl.$^5$ .................. C09K 19/20; C09K 19/12; C07C 69/76
[52] U.S. Cl. .................. 252/299.67; 252/299.65; 252/299.01; 252/299.66; 560/59; 560/65; 560/73; 560/76; 560/83; 560/85; 560/102; 560/108; 560/109
[58] Field of Search .............. 252/299.1, 299.6, 299.61, 252/299.62, 299.63, 299.64, 299.65, 299.66, 299.67; 560/59, 65, 73, 76, 83, 85, 102, 108, 109; 359/10

[56] References Cited

U.S. PATENT DOCUMENTS

| | | | |
|---|---|---|---|
| 4,725,688 | 2/1988 | Taguchi et al. | 252/299.01 |
| 4,780,241 | 10/1988 | Furukawa et al. | 252/299.63 |
| 4,780,242 | 10/1988 | Miyazawa et al. | 252/299.65 |
| 4,876,025 | 10/1989 | Saito et al. | 252/299.61 |
| 4,911,863 | 3/1990 | Sage et al. | 252/299.65 |
| 5,133,896 | 7/1992 | Coates et al. | 252/299.65 |

FOREIGN PATENT DOCUMENTS 8705013  8/1987

Primary Examiner—Robert L. Stoll
Assistant Examiner—Shean C. Wu
Attorney, Agent, or Firm—Nixon & Vanderhye

[57] ABSTRACT

Novel cyanohydrin derivatives of general formula (I) wherein $R^1$ is hydrogen, alkyl, alkoxy, perfluoroalkyl or perfluoroalkoxy, $R^2$ is alkyl, r is 1 to 10, n and m are 0 or 1, provided if both n and m are 0 then X is (II) or (III), where (F) indicates one or more optional fluorines, p is 0 or 1, Z is a single bond if p is 0 and COO is p is 1; and if one or both of n or m are 1 then X is (IV), where each ring A, B and C is phenyl, fluoro- or chlorophenyl, cyclohexyl, pyrimidyl, pyridyl, or dioxanyl, A, B and C are single bonds or linking groups, and (a+b+c) is 2 or 3. Liquid crystal materials containing these compounds are also described.

13 Claims, 6 Drawing Sheets

ROUTE B

ROUTE C

ROUTE D

ROUTE E

ROUTE F

ROUTE G

CYANOHYDRIN DERIVATIVES AND THEIR USE IN LIQUID CRYSTAL MATERIALS AND DEVICES

This is a division of application Ser. No. 07/543,744, filed Jul. 11, 1990, now U.S. Pat. No. 5,133,896.

BACKGROUND OF THE INVENTION

1. Field of Invention

This invention relates to cyanohydrin derivatives and also to liquid crystal materials containing them. In particular the invention relates to chiral derivatives and ferroelectric smectic liquid crystal compositions containing them.

2. Description of the Prior Art

Ferroelectric smectic liquid crystal materials are known, (e.g. N. A. Clark et al: Appl Phy Lett (1980) 36 899), and exploit the electro-optical properties of the ferroelectric chiral smectic phase. The chiral smectic C (abbreviated $S_C^*$ the asterisk denoting chiralty) is most used as it is the most fluid, but other chiral smectic phases e.g. I, F, J, K, G, H or X may also be used.

Although some ferroelectric smectic liquid crystal materials are single compounds it is more usual for such a material to be a composition. Generally such a composition contains one or more compounds which either singly or together shown an $S_C$ phase (termed a smectic "host"), together with one or more chiral (i.e. optically active) compounds which are generally added to induce the smectic material to show a high spontaneous polarisation, Ps. The composition may also contain additives. For example to broaden the Sc* range, to suppress undesirable phases, or optically active compounds to modify the helical pitch of the Sc* phase.

Among the features sought in a good ferroelectric smectic liquid crystal material are low viscosity, fast switching speeds, a broad Sc* phase range, and a high spontaneous polarisation coefficient Ps and a long helical pitch. In view of the high cost of synthesis of optically pure compounds it is also desirable that the chiral compound is cheap.

Optically active compounds used in ferroelectric smectic liquid crystal compositions generally consist of a "core" consisting of a chain of linked cyclic groups, with an optionally active group containing an asymmetric carbon atom at or near a terminal position of the chain. The core is selected from the reasonably well known combinations of cyclic groups which encourage the compound to be miscible with smectic liquid crystal phases. The goal of much research in ferroelectric smectic liquid crystal chemistry is to identify novel optically active groups which may be combined with such cores to form advantageous compounds.

Many suitable optically active compounds are known.

PCT/GB 87/00441 (Agents Ref P0383) and JPA-61-243055 describe compounds of structure

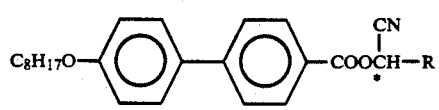

where R is alkyl. These compounds show a high Ps. PCT/GB87/00441 has a publication date later than the priority date of this application.

SUMMARY OF THE INVENTION

It is an object of the present invention to provide novel compounds which are suitable optically active constituents of ferroelectric liquid crystal compositions, and which have advantageous properties relative to known compounds.

This invention provides compounds which are novel cyanohydrin derivatives having a general formula I:

wherein $R^1$ is selected from hydrogen, $C_1$-$C_{12}$ alkyl, alkoxy, perfluoroalkyl and perfluoroalkoxy and may be straight chain or branched chain; $R^2$ is alkyl, which may be $C_1$-$C_8$ straight chain, $C_1$-$C_{15}$ branched chain or cyclic; r is an integer 1 to 10, n and m are independently 0 or 1; with the provisos that:

if both n and m are 0 then X is selected from:

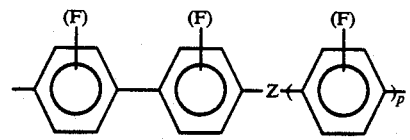

and

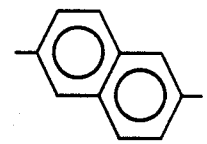

where the (F)'s indicate that X carries one or two fluorine substituents in any one or two of the available lateral substitution positions on the indicated phenyl rings, p is 0 or 1, Z is a single bond where p is 0 and COO when p is 1, and:

if one or both of n or m are 1 then X is a group of general formula:

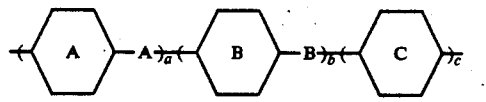

where reach ring A, B and C is independently selected from phenyl, fluoro or chloro substituted phenyl, cyclohexyl, pyrimidyl, pyridyl or dioxanyl, each link A, B and C is indenpendently a single bond, COO, OOC, $CH_2CH_2$, CH=N, N=CH, $CH_2O$, $OCH_2$ or O, and each of a, b and c is 0 or 1 provided (a+b+c) is 2 or 3.

DESCRIPTION OF PREFERRED EMBODIMENTS

The structural preferencies expressed below are on the basis of ease of preparation and/or advantage in liquid crystal compositions, particularly of the ferroelectric type.

Preferred compounds of formula I therefore have a formula II:

$$R^1+CH=CH+CH_2)_r C)_n H+OCH_2)_m COO\overset{*}{C}H-R^2 \quad \overset{CN}{|} \qquad II$$

wherein $R^1$ is selected from $C_1$–$C_{12}$ alkyl or alkoxy; $R^2$, r, n and m are as defined in formula I, with the provisos that:

is both n and m are O then X is selected from:

<img: biphenyl-Z-phenyl structure with (F) substituent> and

<img: naphthalene structure> where p and Z and their relationship are as defined in formula I and (F) indicates that the biphenyl system carries one or two fluorine substituents on any one or two of the available substitutions positions of the biphenyl system, and if one or both of n or m are 1 then X is a group of general formula:

<img: A-B-C ring structure> where each ring A, B and C is indenpendently selected from phenyl, fluoro or chloro substituted phenyl and trans-cyclohexane, c is 0 or 1, B is COO or a single bond, being a single bond if c is 0.

If n and m are not both 0, then preferably one rather than both of n or m is 1. In formula II, X is preferably biphenyl or laterally monofluorosubstituted biphenyl.

Particularly preferred compounds of formula II are those of formula IIA, i.e. a subclass of the case where n and m are both 0.

<img: IIA structure — $R^1$–phenyl(F)–Z–phenyl$_p$–COO$\overset{*}{C}$H(CN)–$R^2$>

IIA where $R^1$ (F), Z, p and $R^2$, and their relationship are as defined in formula II above. Preferably in formula IIA there is one substituent (F), or two in the 2,3 or 2',3' positions on the biphenyl.

Some preferred structural types encompassed by formula IIA are those listed in table 1 below:

TABLE 1

| | |
|---|---|
| IIA1 | $R^1$–(F-phenyl)–phenyl–COO$\overset{*}{C}$H(CN)–$R^2$ |
| IIA2 | $R^1$–(F-phenyl)–phenyl–COO$\overset{*}{C}$H(CN)–$R^2$ |
| IIA3 | $R^1$–phenyl–(F-phenyl)–COO$\overset{*}{C}$H(CN)–$R^2$ |
| IIA4 | $R^1$–phenyl–(F-phenyl)–COO$\overset{*}{C}$H(CN)–$R^2$ |
| IIA5 | $R^1$–(F-phenyl)–phenyl–COO–phenyl–COO$\overset{*}{C}$H(CN)–$R^2$ |
| IIA6 | $R^1$–(F-phenyl)–phenyl–COO–phenyl–COO$\overset{*}{C}$H(CN)–$R^2$ |
| IIA7 | $R^1$–phenyl–(F-phenyl)–COO–phenyl–COO$\overset{*}{C}$H(CN)–$R^2$ |
| IIA8 | $R^1$–phenyl–(F-phenyl)–COO–phenyl–COO$\overset{*}{C}$H(CN)–$R^2$ |
| IIA9 | $R^1$–(F,F-phenyl)–phenyl–COO$\overset{*}{C}$H(CN)–$R^2$ |
| IIA10 | $R^1$–(F,F-phenyl)–phenyl–COO–phenyl–COO$\overset{*}{C}$H(CN)–$R^2$ | of these, formulae IIA1, 2, 3, 4, 9 are particularly preferred.

Another preferred class of compounds of formula II are those of formula IIB:

$$R^1-CH=CH+CH_2)_r O-\text{(F)phenyl}-\text{(F)phenyl}-B+\text{(Q)}_d\text{phenyl})_c COO\overset{*}{C}H(CN)-R^2 \quad IIB$$

wherein $R^1$, r, B, c and $R^2$ are as defined in formula II, (F) indicates that the relevant phenyl ring may carry a fluorine substituent, Q is fluorine or chlorine and d is 0 or 1.

Preferably r in formula IIB is 1 to 6, more preferably 1 to 4.

Some preferred structural types encompassed by formula IIB are those listed in Table 2 below where $R^1$—CH=CH—$(CH_2)_r$—O is abbreviated to RB:

TABLE 2

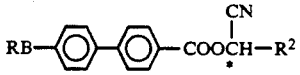 IIB1

 IIB2

 IIB3

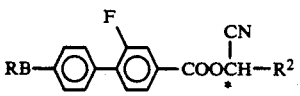 IIB4

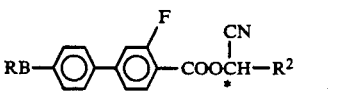 IIB5

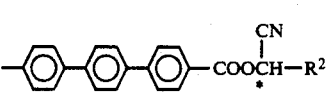 IIB6

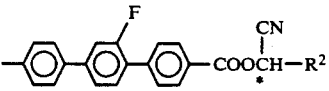 IIB7

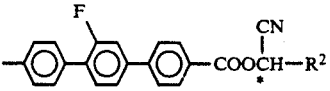 IIB8

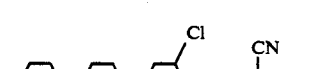 IIB9

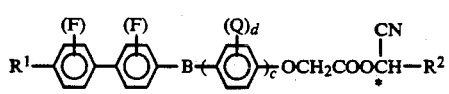 IIB10

Of these, formulae IIB 1, 2 3, 4 and 5 are particularly preferred.

Another preferred class of compounds of formula II are those of general formula IIC, another subclass of formula II where both n and m are 0.

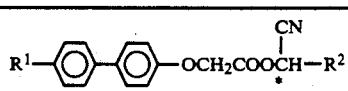 IIC wherein R¹, B, C and R² are as defined in forumla II, (F) indicates that the relevant phenyl ring may carry a fluorine substituent, Q is fluorine or chlorine and d is 0 or 1. Some preferred structural types encompassed by formula IIC are those listed in Table 3 below:

TABLE 3

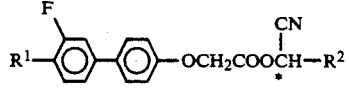 IIC1

TABLE 3-continued

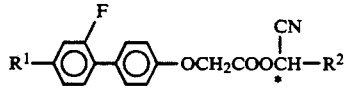 IIC2

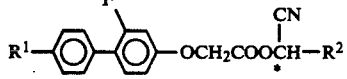 IIC3

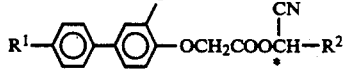 IIC4

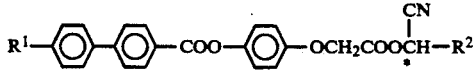 IIC5

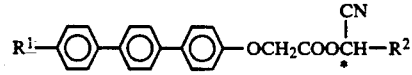 IIC6

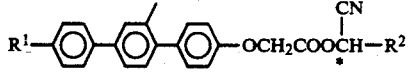 IIC7

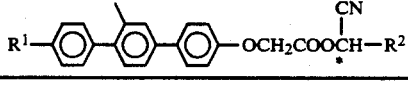 IIC8

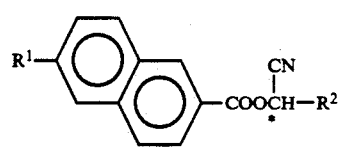 IIC9

Of these, formulae II C1, 2, 3, 4 and 5 are particularly preferred.

A fourth class of preferred compounds of formula II are those of formula IID:

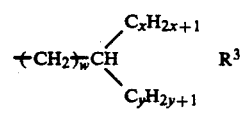 IID where R¹ and R² are as defined in formula II above.

In all the formulae listed above the following preferences apply. R¹ is preferably n-alkyl or n-alkoxy containing 3 or 11 carbon atoms, especially 5 to 9 carbon atoms. R² is preferably $C_1$-$C_5$ n-alkyl especially methyl, cyclohexyl, or in particular a branched or asymmetrically substituted alkyl group R³ of formula:

$$\text{\textendash}(CH_2)_w\text{\textendash}CH\begin{array}{c}C_xH_{2x+1}\\ \\ C_yH_{2y+1}\end{array} \quad R^3$$

where w is 0 or an integer 1 to 5, and each of x and y are independently 1 to 6. Preferably w is 0, and preferably at least one of x and y is 1. R³ may be optically active or in a racemic mixture.

In the above formulae, the carbon atom inidcated by an asterisk in formula I may be present in an optically active form or as a racemic mixture.

Preferred structures for $R^3$ are listed blow in table 4, the most preferred being underlined.

TABLE 4

| | | |
|---|---|---|
| <u>CH<sub>3</sub></u> | CH(CH<sub>3</sub>)<sub>2</sub> | CH<sub>2</sub>CH(CH<sub>3</sub>)<sub>2</sub> |
| C<sub>2</sub>H<sub>5</sub> | <u>CH(CH<sub>3</sub>)C<sub>2</sub>H<sub>5</sub></u> | CH<sub>2</sub>CH(CH<sub>3</sub>)C<sub>2</sub>H<sub>5</sub> |
| C<sub>3</sub>H<sub>7</sub> | CH(CH<sub>3</sub>)C<sub>3</sub>H<sub>7</sub> | CH<sub>2</sub>CH(CH<sub>3</sub>)C<sub>3</sub>H<sub>7</sub> |
| <u>C<sub>4</sub>H<sub>9</sub></u> | CH(CH<sub>3</sub>)C<sub>4</sub>H<sub>9</sub> | CH<sub>2</sub>CH(CH<sub>3</sub>)C<sub>4</sub>H<sub>9</sub> |
| C<sub>5</sub>H<sub>11</sub> | CH(CH<sub>3</sub>)C<sub>5</sub>H<sub>11</sub> | CH<sub>2</sub>CH(CH<sub>3</sub>)C<sub>5</sub>H<sub>11</sub> |
| C<sub>6</sub>H<sub>13</sub> | CH(CH<sub>3</sub>)C<sub>6</sub>H<sub>13</sub> | CH<sub>2</sub>CH(CH<sub>3</sub>)C<sub>6</sub>H<sub>13</sub> |
| C<sub>7</sub>H<sub>15</sub> | CH(CH<sub>3</sub>)C<sub>7</sub>H<sub>15</sub> | CH<sub>2</sub>CH(CH<sub>3</sub>)C<sub>2</sub>H<sub>15</sub> |
| C<sub>8</sub>H<sub>17</sub> | CH(CH<sub>3</sub>)C<sub>8</sub>H<sub>17</sub> | CH<sub>2</sub>CH(CH<sub>3</sub>)C<sub>8</sub>H<sub>17</sub> |
| C<sub>9</sub>H<sub>19</sub> | CH(CH<sub>3</sub>)C<sub>9</sub>H<sub>19</sub> | CH<sub>2</sub>CH(CH<sub>3</sub>)C<sub>9</sub>H<sub>19</sub> |
| <u>C<sub>10</sub>H<sub>21</sub></u> | CH(CH<sub>3</sub>)C<sub>10</sub>H<sub>21</sub> | |

The invention also includes the use of compounds of formula I in liquid crystal compositions, and a liquid crystal composition which includes one or more compounds of formula I. The liquid crystal composition is preferably a smectic C ($S_C$) liquid crystal composition, especially a ferroelectric chiral $S_C$ composition. Preferred compounds of formula I for use in such compositions are as discussed above.

Compounds of formula IIA in an optically active form, preferably those of formulae IIA1, 2, 3 and 4, and especially those of formula IIA1 where $R^1$ is n-alkoxy are particularly useful components of ferroelectric smectic liquid crystal compoistions. they generally have lower melting points, higher solubilities in $S_C$ materials, and when included in such a composition generally lead to a higher spontaneous polarisation Ps, than their unfluorinated counterparts e.g. as described in the cited prior art. These are useful and unexpected advantages.

Compounds of formulae IIB, IIC and IID are also useful components of ferroelectric smectic liquid crystal compositions. One use to which they may be put is that of "pitch compensators" as defined below with compounds of formula IIA.

A ferroelectric smectic liquid crystal compositions of this invention as well as one or more compounds of formula I also contains one or more "host" compounds which either separately or together show an $S_C$ phase. Many such host compounds are known. Preferred host compounds are the known compounds of formula III:

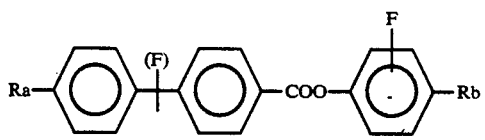

where Ra and R are independently $C_3$–$C_{12}$ alkyl or alkoxy and (F) indicates that the biphenyl system may carry a lateral fluorine substituent. Preferred compounds of formula III are those of forumula IIIA below, i.e. those described in PCT/G86/0040:

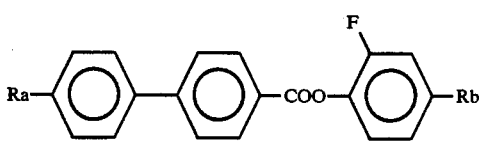

Other preferred host compounds are the known fluoro- and difluoroterphenyls of general formula IV

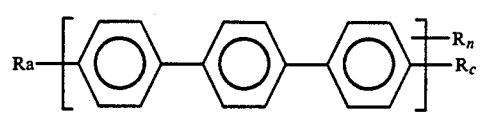

where n is 1 or 2 and Ra and Rb are independently $C_3$–$C_{12}$ alkyl or alkoxy. Preferred terphenyls of foruma IV are those described in EPA 8430494.3 of formula IV A:

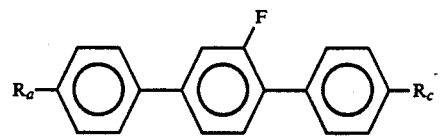

and those described in GB-A-8806220 of formula IV B:

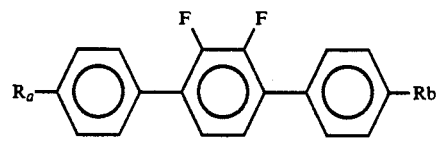

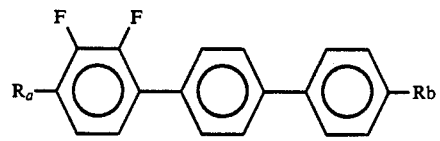

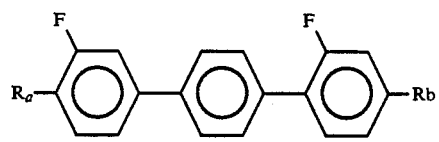

Preferably both Ra and Rb in formulae III and IV are n-alkyl or n-alkoxy.

Other host compounds include cyanocyclohexanes of formula V:

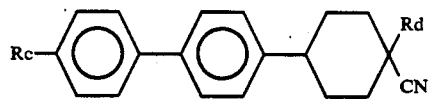

and phenyl pyrimidines of forumula VI:

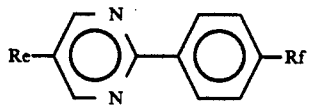

where Rc, Re and Rf are independently $C_3$–$C_{12}$ n-alkyl or alkoxy and Rd is n-alkyl.

As well as containing one or more host compounds, the ferroelectric smectic liquid crystal compoisiton of this invention may also contain additives. These may for example be addivites which broaden the temeprature range over which the Sc phase persists, e.g. known compounds of formula VII:

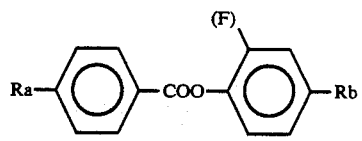

VII where Ra and Rb are independently $C_1$ to $C_{12}$ alkyl or alkoxy and (F) indicates a fluorosubstituent may be present. Additives of formula VII are particularly useful when the host is or includes compounds of formula III or III A. Useful additives when the host is a terphenyl of formula IV, IVA, or IVB are the cyano-terphenyls of general formula VIII:

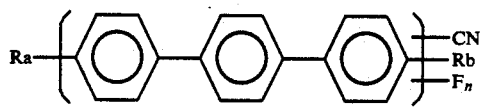

VIII where n is 0 or 1 and Ra and Rb are independently $C_3$-$C_{12}$ n-alkyl or n-alkoxy. Compounds of formula VIII are described in PCT/GB88/

Preferred additives of formula VIII have a formula VIII A:

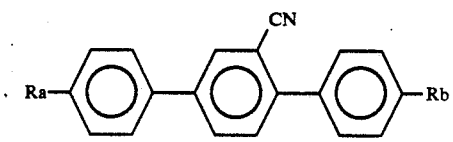

VIIIA and are useful in suppressing $S_B$ phases.

As well as containing these additives the ferroelectric smectic liquid crystal composition of this invention may also contain additives which are "pitch compensators" if the compound of formula I is in an optically active form. Pitch compensators are optically active compounds which have a twisting effect on the $S_C$ phase which is of opposite handedness to that of the optically active compound of formula I. Some examples of pitch compensating additives are the compounds described in PCT/GB87/00223, e.g. IX:

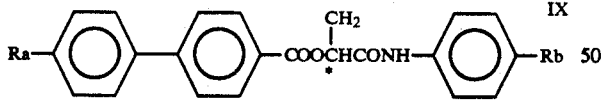

IX where Ra and Rb are independently $C_1$-$C_{12}$ n-alkyl or n-alkoxy. If at least one of the optically active compounds of formula I is a compound of formula IIA, then pitch compensating additives may be compounds of formula IIB, IIC or IID.

In an alternative and preferred method of pitch compensation, two or more compounds each of any one of formulae IIa, IIB, IIC or IID, preferably of formula IIA, having twisting effects of opposite handedness may be used. For example two compounds of the same formula IIA but having the carbon atom indicated by * in formula I in mirror image configurations may be used.

By using pitch compensation the helical pitch of the ferroelectric smectic liquid crystal phase may be adjusted to provide a long pitch.

The ferroelectric liquid crystal composition of this invention typically but no exclusively has the following composition, expressed in weight percentages.

| Host compound(s) | 30–99 | preferably 50–90 |
| Additive(s) | 0–30 | preferably 0–20 |
| Compound(s) of formula I | 5–50 | preferably 5–30 |

Such a ferroelectric smectic liquid crystal composition may be used in any of the known types of liquid crystal device suitable for such a composition, for example the "Clark-Lagerwall Device" described in Appl Phy Lett (1980), 36, 899. The physics of this device and methods of constructing and using one are well known.

BRIEF DESCRIPTION OF THE DRAWINGS

The invention will now be described by way of example only with reference to.

Compounds of formula IIA may be prepared by a number of synthetic routes, but it is preferred to start from the acid X:

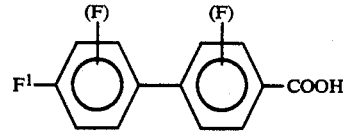

X

Figure 1:
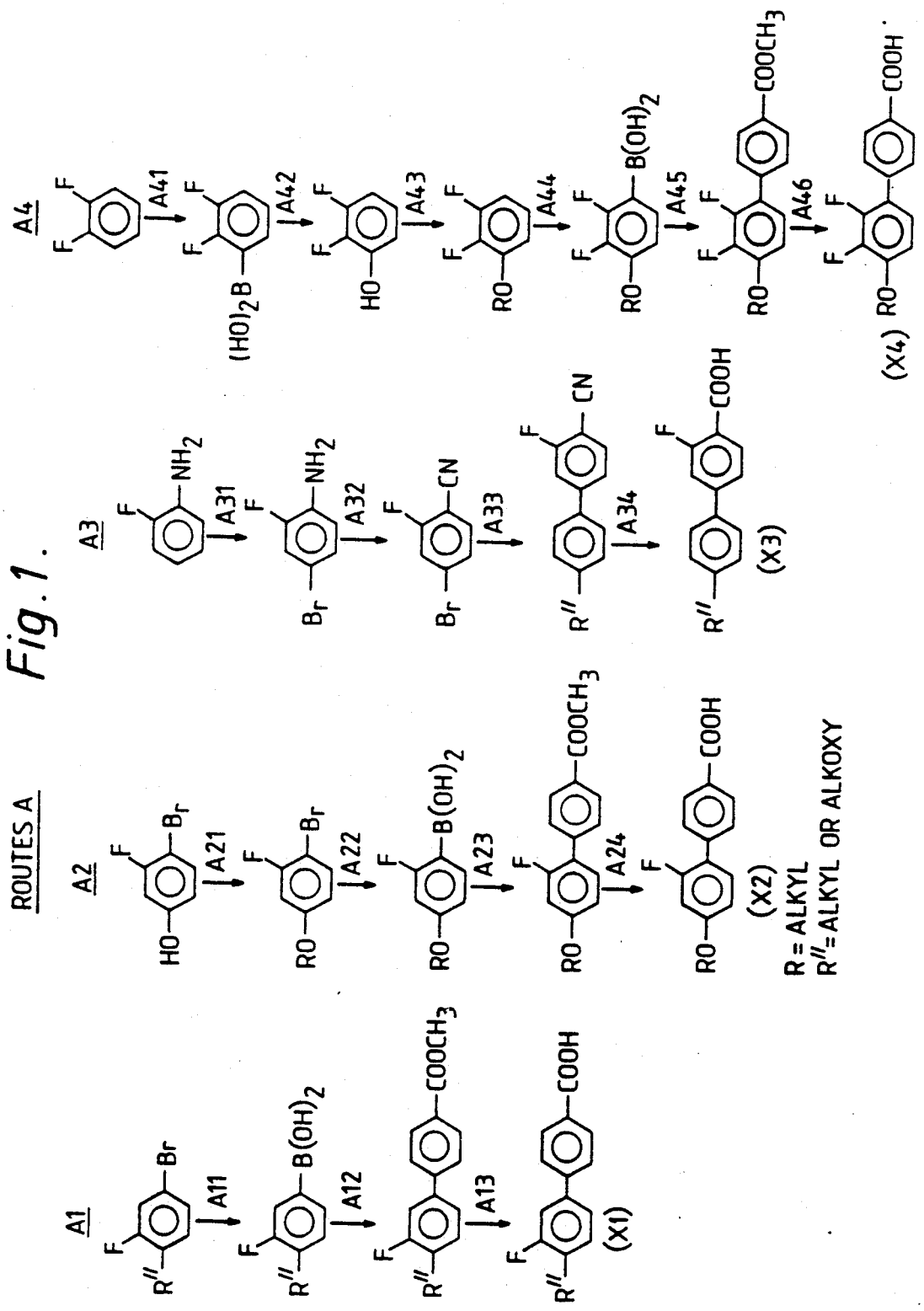
FIG. 1 which shows preparative routes A1 to A4
FIG. 2 which shows preparative routes B
FIG. 3 which shows preparative routes C
FIG. 4 which shows preparative routes D
FIG. 5 which shows preparative routes E
FIG. 6 which shows preparative routes F
FIG. 7 which shows preparative routes G
FIG. 8 which shows a cross section through a liquid crystal device.

Such acids may be commercially available, or else they may be prepared by for example routes A1 to A4 shown in FIG. 1 starting from known compounds, yielding the acids X1, X2, X3 and X4:

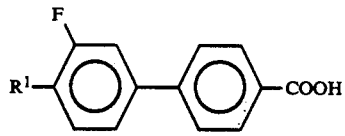

X1

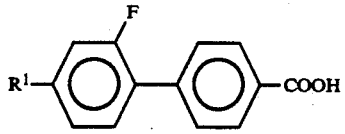

X2

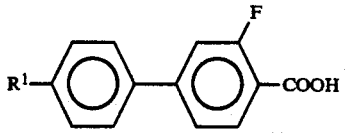

X3

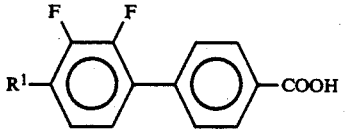

X4

The steps in routes A1, A2, A3 and A4 are:

| | |
|---|---|
| Steps AII, A22 | THF solvent, Mg, triisopropyl borate |
| Steps A12, A23 A33 | Ethanol solvent, palladium (triphenylphosphine): toluene, methyl 4-bromoacetate, 2 M sodium carbonate. |
| Steps A13, A24 A34 | Hydrolysis, ethanol sodium hydroxide: $H_2SO_4$. |
| Step A21 | 1-bromoalkane, acetone, potassium carbonate. |
| Step A32 | Diazotisation, KCN |
| Step A41 | butyl lithium / $-70°$ C. / $B(OCH_3)_3$ reacted with the lithium Grignard reagent. |
| Step A42 | Hydrogen Peroxide |
| Step A43 | RBr / butanone / potassium carbonate / reflux |
| Step A44 | as step A41. |
| Step A45 | palladium (triphenylphosphine) / toluene/ sodium carbonate / methyl-4-bromobenzoate. |
| Step A46 | potassium hydroxide/ IMS / reflux 2 hours. |

Figure 2:
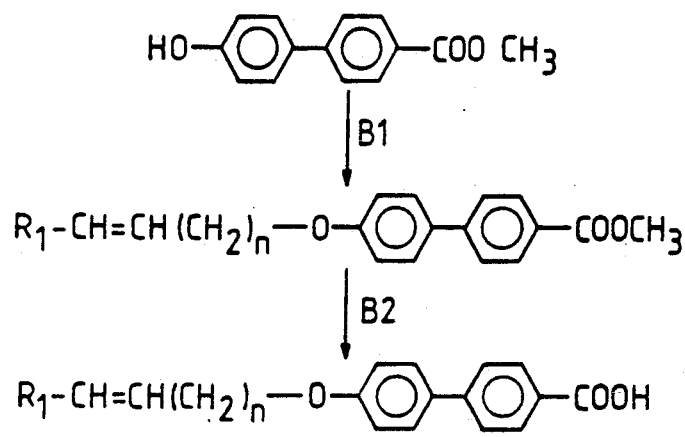

Compounds of formula IIB may be prepared by a number of synthetic routes, but it is preferred to start from the acid XI:

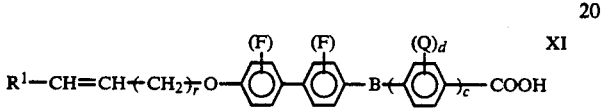

which may be prepared by route B shown in FIG. 2. This route is of general applicability for use with any appropriate hydroxy-ester.

In route B the steps are as follow:

| | |
|---|---|
| B1 | Bromoalkene, butanone solvent, $K_2CO_3$. |
| B2 | Potassium hydroxide, water/methylated spirit. |

Figure 3:
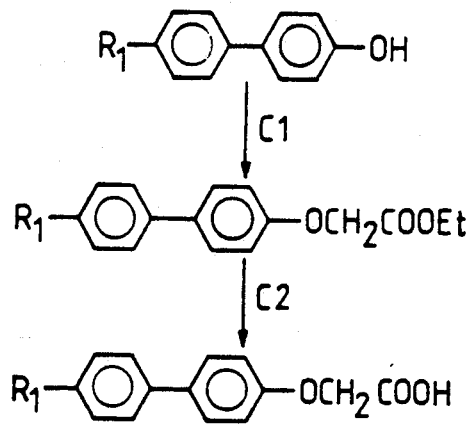

Compounds of formula IIC may be prepared by a number of synthetic routes, but it is preferred to start from the acid XII:

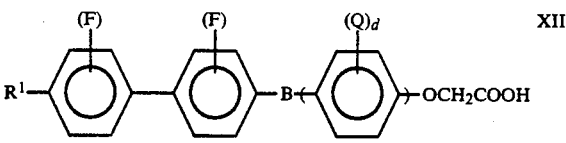

which may be prepared by route C shown in FIG. 3. This route is of general applicability to any phenol or alcohol. In route C the steps are as follows:

| Route C | |
|---|---|
| C1 | Ethylbromoacetate, potassium carbonate, butanone solvent. |
| C2 | KOH, water, 2-methoxyethanol, ethanol. |

Compounds of formula IID may be prepared using the known naphthoic acids.

These acids may then be esterified with an appropriately protected alpha-hydroxy acid, deprotected and converted into the nitrile.

Figure 4:
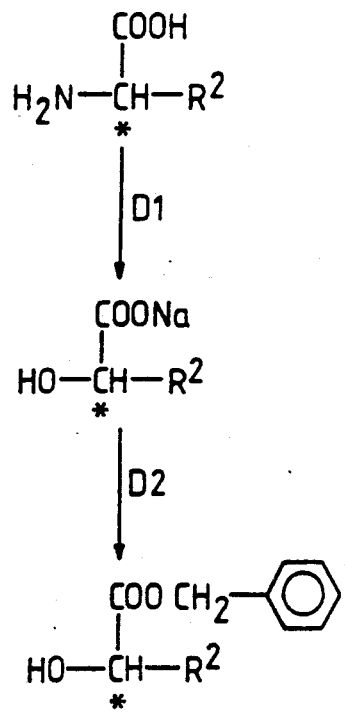
Figure 5:
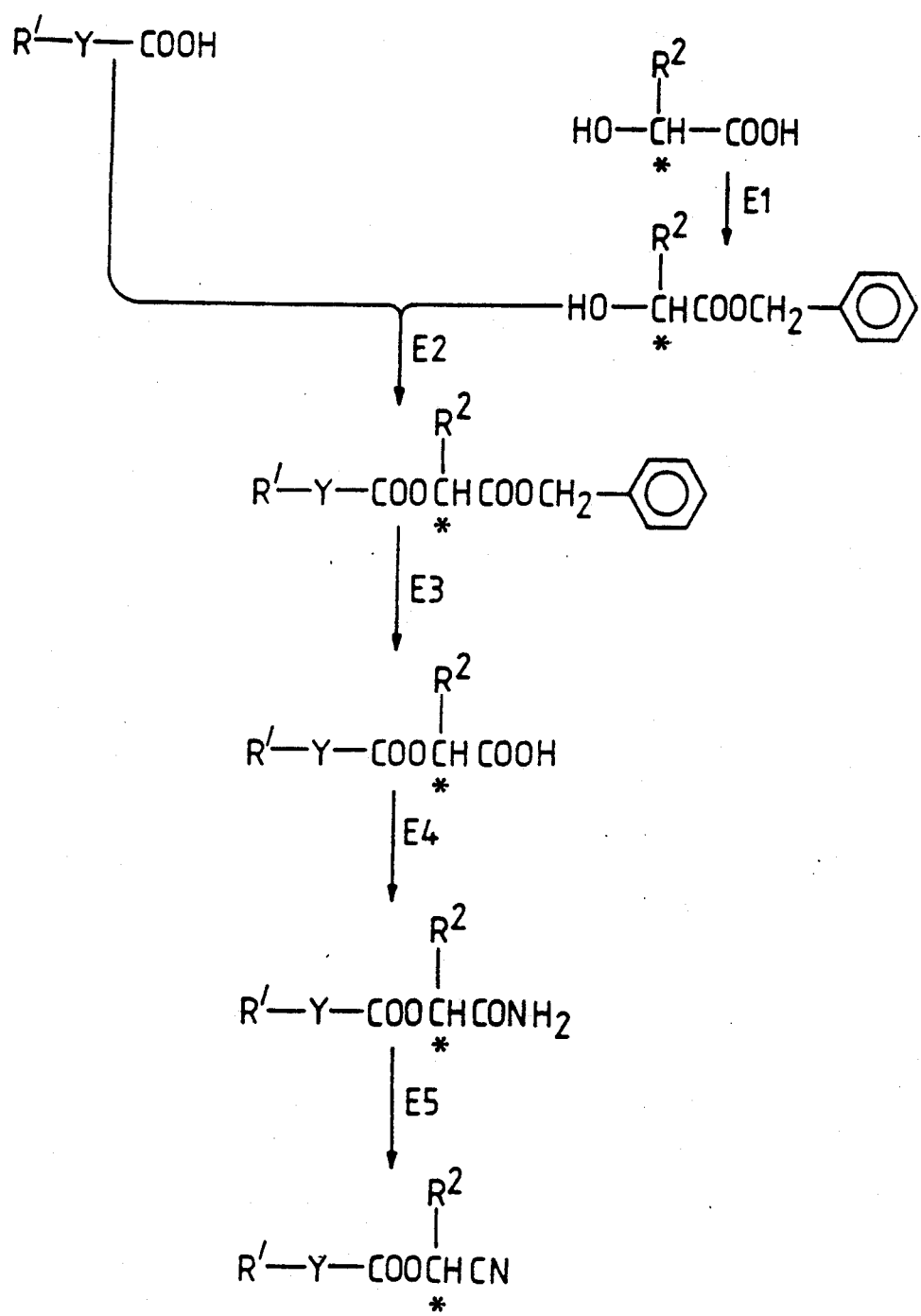
Figure 6:
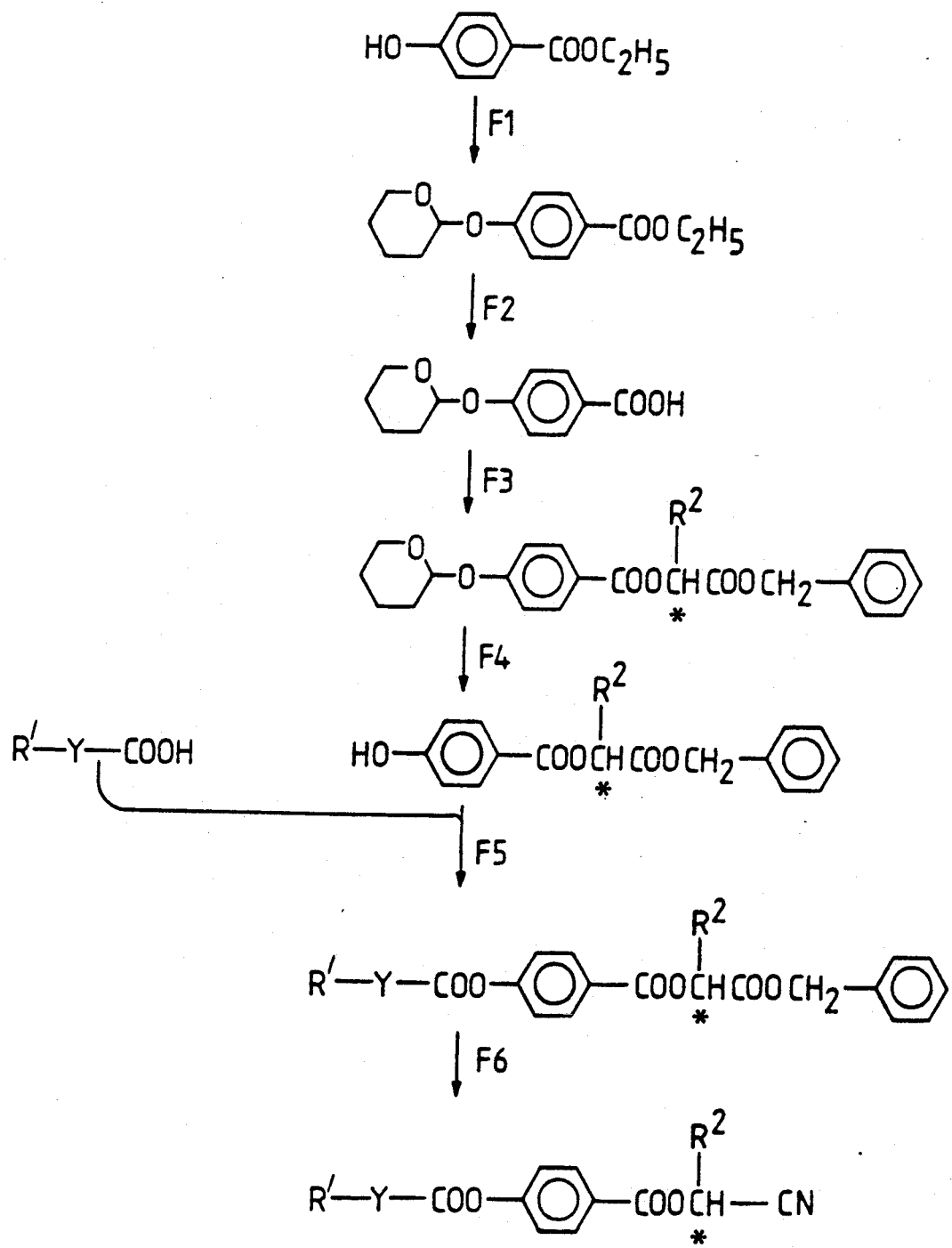
Figure 7:
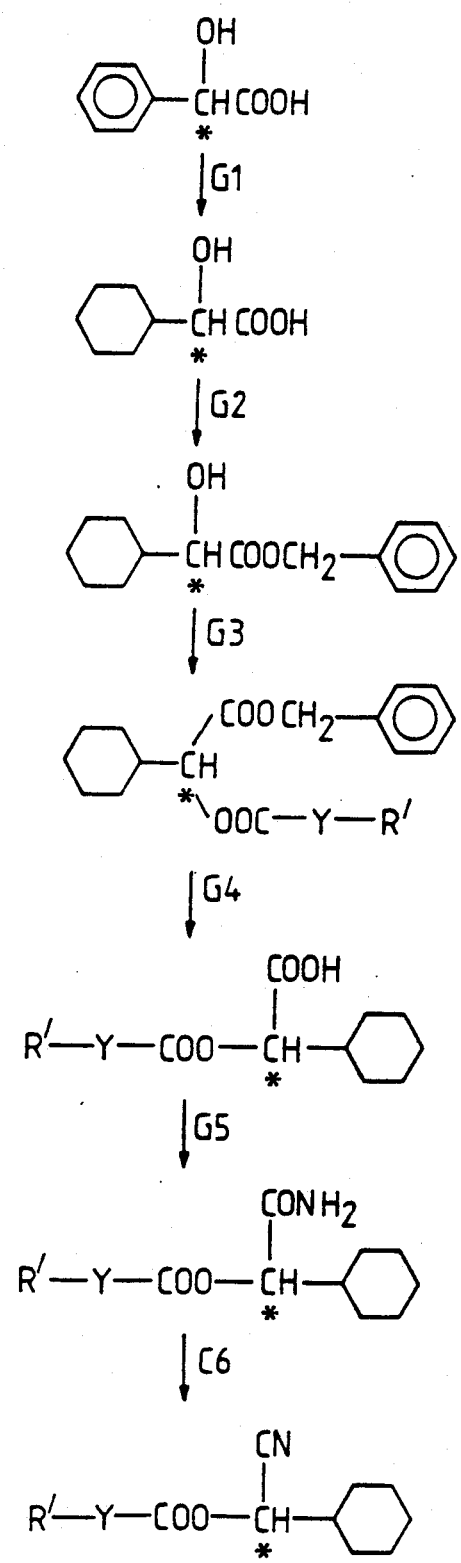

Suitable routes are routes E, F and G in FIGS. 5, 6 and 7. Many alpha-hydroxy carboxylic acids $HO-CH(R_2)COOH$ for use in these routes are commercially available, e.g. lactic acid and mandelic acid. Alternatively one may start from an alpha amino acid such as valine as shown in FIG. 4 route D using the following steps:

| | |
|---|---|
| D1 | Sodium Nitrite, $H_2SO_4$. |
| D2 | (a) $K_2CO_3$, methanol-water 9:1 pH7 |
| | (b) benzyl bromide, DMF |

The individual steps of routes 5, 6 and 7 are as follows:

| Route E | |
|---|---|
| E1 | As step D2 |
| E2 | N,N-dicyclohexyl carbodiimide (DCC), 4-(N-pyrrolidino)pyridine (N—PPy) $CH_2Cl_2$ |
| E3 | 5% Pd/C, hydrogen, ethanol |
| E4 | (a) oxalyl chloride, benzene, DMF |
| | (b) aqueous ammonia, diglyme |
| E5 | $SOCl_2$, DMF |

| Route F | |
|---|---|
| F1 |  ethyl acetate, hydrogen chloride |
| F2 | KOH, ethanol, water |
| F3 | as step D2 |
| F4 | oxalic acid, 90% aqueous ethanol |
| F5 | as step E2 |
| F6 | a series of steps analogous to steps E3-E5 |

| Route G | |
|---|---|
| G1 | hyrogen, 5% $Rh/Al_2O_3$, methanol (starting compound: mandelic acid) |
| G2 | as step D2 using methanol solvent |
| G3 | DCC, N—PPy, $CH_2Cl_2$ |
| G4 | hydrogen, 5% Pd —C, ethanol |
| G5-G6 | as steps E4 and E5 |

Related routes may be used to prepare other compounds of formula IIA.

In routes E, F and G, Y represents the particular group between $R^1$ and COO in formula I, for example Y may be:

in the preferred formula II compounds discussed above.

The invention will now be described by way of example only, with reference to FIGS. 1-7 which shown preparative routes for compounds of formula I; and FIG. 8 which shows a cross sectional view through a liquid crystal display device.

Abbreviations

C=solid crystal
N=nematic liquid crystal
S_C=smectic C
S_A=smectic A
I=isotropic liquid All temperatures (melting point, boiling point, liquid crystal transitions, e.g. C-I, are in degrees centigrade).

EXAMPLE 1

Routes A1 and E to prepare:

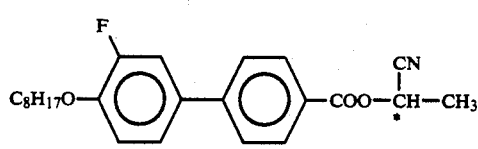

Steps A11-A13

3'-fluoro-4'-octoxybiphenyl-4-carboxylic acid was first prepared by the following method: 4-Bromo-2-fluorooctoxybenzene (95 g) (made by standard bromination of 2-fluorooctoxybenzene) was dissolved in dry tetrahydrofuran (250 ml) and slowly added to a mixture of magnexium turnings (8.5 g) and tetrahydrofuran (50 ml) containing a crystal of iodine. The Gagnard reaction was initiated by heating the solution. After the addition of bromide solution the mixture was stirred and refluxed under nitrogen for one hour. this solution was then transferred via a flexi-needle into a solution of triisopropylborate (123 g) in tetrahydrofuran (10 ml) at −70° C. in a nitrogen atmosphere over 30 minutes. The mixture was then allowed to warm up to room temperature over 3 hours. 10% HCL was added to the mixture and the organic layer separated, washed with brine, dried and solvent removed. The crude solid was dried in vacuo at 20° C. Yield 80.4 g.

The product (32.2 g) in methylated spirits (50 ml) was added to a mixture of palladium tetra (triphenylphosphine) (0.6 g), tolvene (200 ml), methyl 4-bromobenzoate (21.5 g) and a 2M solution of sodium carbonate (100 ml). The mixture was heated under reflux and stirred vigorously for 16 hours. After cooling, the reaction mixture was poured into water and the organic layer separated. The aqueous layer was extracted twice with toluene and the combined organic layers washed once with water. The solvent was removed, and the dark brown solid chromatographed on alumina (100 g) using a mixture of dichloroemthane and petroleum ether. Yield 46.9 g. After crystallisation from methylated spirits the yield was 24.4 g: mp 90° C. HPLC 99.9%.

Step E1

S-(+)- lactic acid (200 g) was dissolved in 90 % aqueous methanol (2000 ml) and treated with 20% aqueous sodium carbonate until the pH was 7. The solvent was removed at 50° C. under vaccuum and then azeotropically removed using dichloroemthane (600 ml). The lactic acid potassium salt was dissolved in dry dimethyl formamide (12 ml) and benzyl bromide (278 ml) added over 30 minutes. This solution was stirred for 16 hours. Solvent was removed under vacuum at 40°-50° C., water (600 ml) was added and the product was extracted into ether. After drying over sodium sulphate the ether layer was distilled to yield a colourless oil bp 88°-90° C. at 0.5 mm Hg/Yield 279 g, 70%, glc 99.2%.

Step E2

The product from Step A13 (10 g) was stirred for 16 hrs with dry tolune (120 ml), oxalyl chloride (12.4 g) and ten drops of dry DMF. The toluene was distilled off and the acid chloride and redissolved in toluene (40 mls) and added to the product from Step E1 (4.41 g) a pyridine (20 mls). The mixture was stirred for 30 minutes at 20° C. then heated under reflux for 3 hours. After cooling the solution was carefully neutralized with dilute hydrochloric acid, the organic layer was removed and washed with sodium bicarbonate solution, then water. After drying, the organic layer was chromatographed on aluminium. Yield 65% after crystallisation from IMS.

Step E3

The product from Step E2 (8.2 g) was dissolved in ethyl acetate (65 mls). 5% Pd on carbon (1 g) was added and the mixture stirred under a hydrogen atmosphere overnight. The catalyst was filtered off and the solution evaporated and the white solid dried under vacuum. Yield 98%.

Step E4

The product from Step E3 (5 g) was stirred at 20° C. with tolvene (100 ml), DMF (10 drops) and oxalyl chloride (2.87 g) for 3 hrs. The solvents were removed and the acid chloride dissolved in day dichloromethane (100 mls). To this solution was added a mixture of dichloromethane (100 ml) and conc ammonia solution (1.5 ml) over about 10 minutes. After a further 10 minutes stirring at 20° C., water (200 mls) was added and the solution separated. The organic layer yielded 4 g of a white solid. This was dried at 40° C. under vacuum and used in the next step.

Step E5

DMF (8 ml) was added to thionyl chloride (10.7 g), and the product from Step E4 (4 g), dissolved in dimethylformamide (40 ml), was added to the cooled thionyl chloride solution. This mixture was stirred at 10.75° C. for 2 hours and then ice/water (200 g) was added. The product was isolated by extraction into ether followed by chromatography on silica gel. After crystallation from heptane a white solid was obtained. Yield 2.8 g. The product showed C-I transition at 56° C.

MIXTURE EXAMPLE 1

A ferroelectric smectic liquid crystal mixture was prepared which consisted of a 10 weight % solution of the product of Step E5 in:

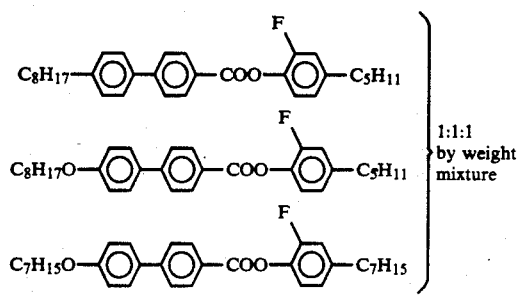

1:1:1 by weight mixture

This composition had the following properties:

| (1) | Liquid crystal transitions: |
|---|---|
| | Sc at room temperature and below |
| | $S_C$—$S_A$ 83° C. |
| | $S_A$—N 109.6° C. |
| | N—I 137.140° C. |
| (2) | Ferroelectric properties: |

| Temp (°C.) | Ps (nC cm$^{-2}$) | Tilt (°) |
|---|---|---|
| 80 | 3.39 | |
| 75 | 9.67 | 21.5 |
| 70 | 14.11 | |
| 65 | 17.78 | |
| 60 | 20.67 | |
| 55 | 23.56 | 22.0 |
| 50 | 26.67 | |
| 40 | 33.33 | |

The extrapolated Ps of the cyanohydrin compound, deduced from this composition, 20° C. below the $S_C$-$S_A$ transition was 190 nCcm$^{-1}$.

EXAMPLE 2

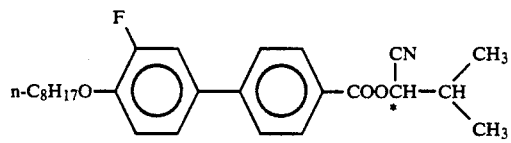

was prepared using the acid prepared in steps A11–A13 of Example 1 above, and route D. The experimental conditions for route D were the same as used for steps 4(1) and 4(2) of Example 5 on page 31 of WO 87/07890. C-I=50° C. The extrapolated Ps value of a 10 wt % solution in the same liquid crystal host as used in mixture Example 1 was 250 nCcm$^{-1}$ 20° C. below the $S_C$-$S_A$ transition temperature. In a host mixture consisting of a 1:1:1:1 ratio of terphenyls of formula

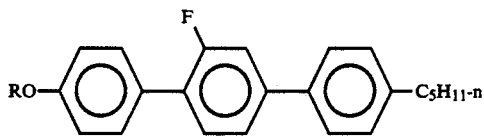

where R was $C_6H_{13}$, $C_8H_{17}$, $C_7H_{15}$ and $C_{10}H_{21}$ (all n-) the extrapolated Ps was 236 nCcm$^{-1}$.

Using analogous methods, compounds of analogous structure but where $R^3$ was $CH_2CH(CH_3)_2$, $CH(CH_2)C_3H_5$ and $(CH_2)_3CH$, starting from L-leucine, L-isoleucine, and L-norleucine were prepared.

The following results compare the solubility of the compounds of examples 1 and 2 in the host mixture used in mixture example 1, their melting points, and their extrapolated Ps values at 20° C. below $S_C$-$S_A$, with the corresponding values for their unfluorinated analogues.

| Compound | soly. | mpt. | ext. Ps |
|---|---|---|---|
| n-C$_8$H$_{17}$O—[F-ring]—[ring]—COOCHCH$_3$(CN) | 10% | 56 | 190 |
| n-C$_8$H$_{17}$O—[ring]—[ring]—COOCHCH$_3$(CN) | | 126 | |
| n-C$_9$H$_{19}$O—[ring]—[ring]—COOCHCH$_3$(CN) | 10% | 98 | 170 |
| n-C$_8$H$_{17}$O—[F-ring]—[ring]—COOCHCH(CH$_3$)$_2$(CN) | 15% | 50 | 250 |
| n-C$_8$H$_{17}$O—[ring]—[ring]—COOCHCH(CH$_3$)$_2$(CN) | | 67 | 164 |
| n-C$_9$H$_{19}$O—[ring]—[ring]—COOCHCH(CH$_3$)$_2$(CN) | 10% | 67 | 170 |

Two more mixture examples are given below using compounds of examples 1 and 2, and taking advantage of their high solubility:

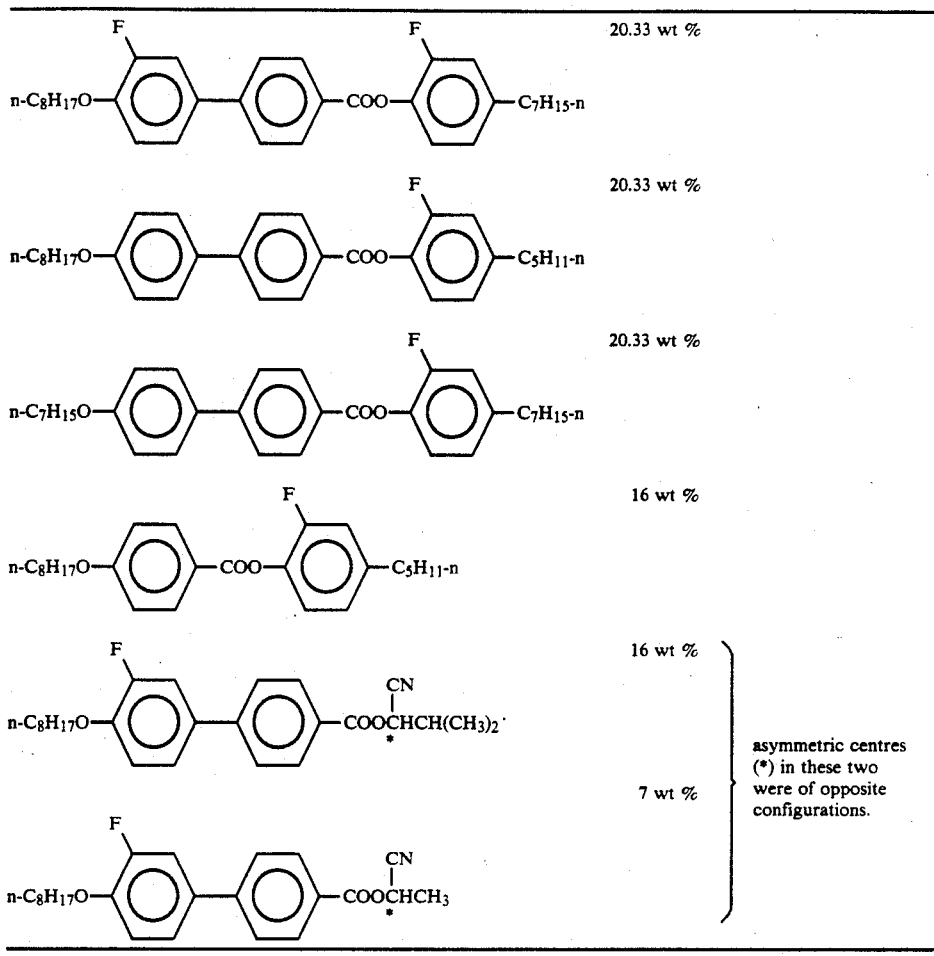
This mixture showed: $S_C$—$S_A$ 28° C., $S_A$—N 73° C. N—I 88.6° C.
Ps at 18° C. = 46 nCcm$^{-1}$
Ps at 8° C. = 66 nCcm$^{-1}$
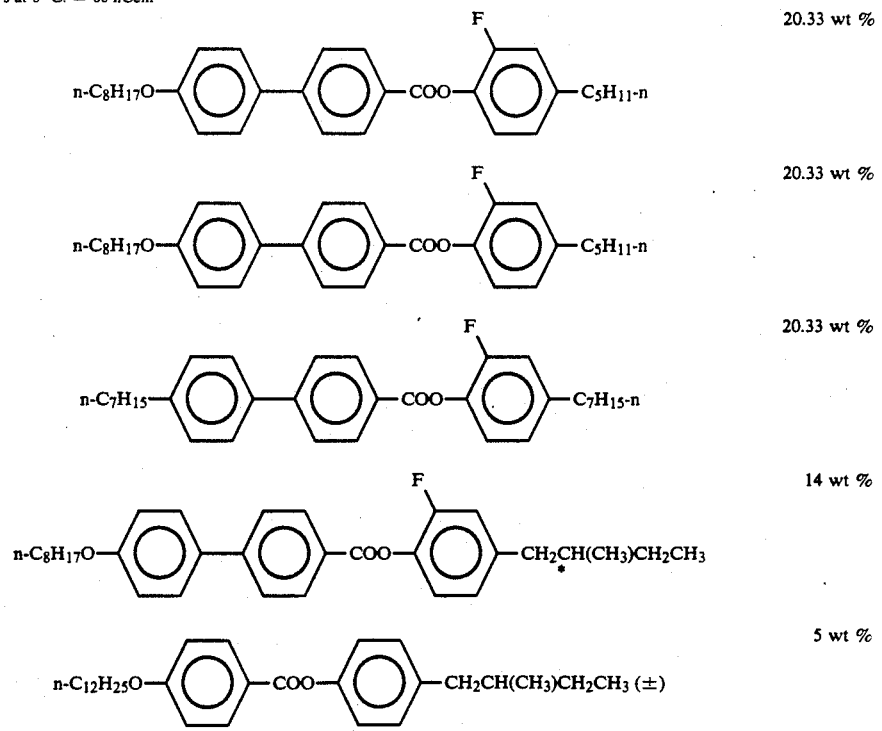

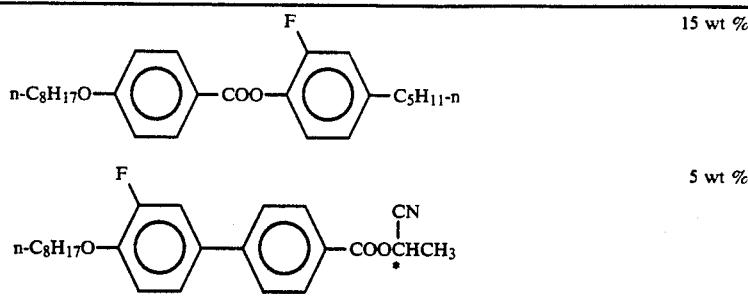

| | |
|---|---|
| n-C$_8$H$_{17}$O—⟨○⟩—COO—⟨○⟩(F)—C$_5$H$_{11}$-n | 15 wt % |
| n-C$_8$H$_{17}$O—⟨○⟩(F)—⟨○⟩—COOCH(CN)CH$_3$ | 5 wt % |

This mixture showed: $S_C$—$S_A$ = 62.4° C., $S_A$—N = 84.0° C., N—I = 117.6° C.
Ps at 30° C. = 16.46 nC cm$^{-1}$

EXAMPLE 3

Routes B and E

Preparation of:

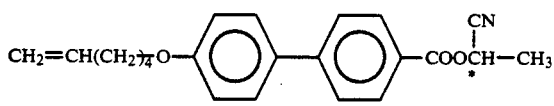

CH$_2$=CH(CH$_2$)$_3$O—⟨○⟩—⟨○⟩—COOCH(CN)—CH$_3$

Step B1

Methyl 4-hydroxybiphenyl-4-carboxylate (17 g), bromopentene (12.7 g) butanone (200 ml) and anhydrous potassium carbonate (22 g) were stirred and heated under reflux for 16 hrs. The colled solution was filtered, and the solid washed with acetone (1001 l). The combined filtrates were evaporated to dryness, taken up in dichloromethane (200 ml), washed with water (2×50 l), dried over sodium sulphate and evaporated to dryness. The solid was crystallised from methylated spirits. Yield 20 g.

Step B2

The product from Step B1 (19.5 g) was stirred and heated under reflux for 2 hours with potassium hydroxide (8.4 g), water (30 ml) and methylated spirits (100 ml). The solution was poured into water (100 mls) and acidified wity cony Hce. The solid was filtered off, washed with water and dried in vacuo. After crystallisation from acetic acid a yield of 15 g was found. HPLC 99.6%.

Step E1

S-(+)- lactic acid (200 g) was dissolved in 90% aqueous methanol (2000 ml) and treated with 20% aqueous sodium carbonate until the pH was 7. The solvent was removed at 50° C. under vaccuum and then azeotropically removed using dichloromethane (600 ml). The lactic acid potassium salt was dissolved in dry dimethyl formanide (12 ml) and benzyl bromide (278 ml) added over 30 minutes. This solution was stirred for 16 hours. Solvent was removed under vacuum at 40°-50° C., water (600 ml) was added and the product was extracted into ether. After drying over sodium sulphate the ether layer was distilled to yield a colourless oil bp 88°-90° C. at 0.5 mm Hg/Yield 279 g, 70%, glc 99.2%.

Step E2

The product from Step B2 (10 g) was stirred for 16 hrs with dry tolune (120 ml), oxalyl chloride (12.4 g) and ten drops of dry DMF. The toluene was distilled off and the acid chloride and redissolved in toluene (40 mls) and added to the product from Step E1 (4.41 g) a pyridine (20 mls). The mixture was stirred for 30 minutes at 20° C. then heated under reflux for 3 hours. After cooling the solution was carefully neutralised with dilute hydrochloric acid, the organic layer was removed and washed with sodium bicarbonate solution, then water. After drying, the organic layer was chromatographed on aluminium. Yield 65% after crystallisation from IMS.

Step E3

The product from Step E2 (8.2 g) was dissolved in ethyl acetate (65 mls). 5% Pd on carbon (1 g) was added and the mixture stirred under a hydrogen atmosphere overnight. The catalyst was filtered off and the solution evaporated and the white solid dried under vacuum. Yield 98%.

Step E4

The product from Step E3 (5 g) was stirred at 20° C. with tolvene (100 ml), DMF (10 drops) and oxalyl chloride (2.87 g) for 3 hrs. The solvents were removed and the acid chloride dissolved in day dichloromethane (100 mls). To this solution was added a mixture of dichloromethane (100 ml) and cone ammonia solution (1.5 ml) over about 10 minutes. After a further 10 minutes stirring at 20° C., water (200 mls) was added and the solution separated. The organic layer yielded 4 g of a white solid. This was dried at 40° C. under vacuum and used in the next step.

Step E5

DMF (8 ml) was added to thionyl chloride (10.7 g), and the product from Step E4 (4 g), dissolved in dimethylformamide (40 ml), was added to the cooled thionyl chloride solution. This mixture was stirred at 10.75° C. for 2 hours and then ice/water (200 g) was added. The product was isolated by extraction into ether followed by chromatography on silica gel. After crystallation from heptane a white solid was obtained. Yield 2.8 g.

MIXTURE EXAMPLE 3

A ferroelectric smectic liquid crystal mixture was prepared which consisted of a 10 weight % solution of the product of Step in:

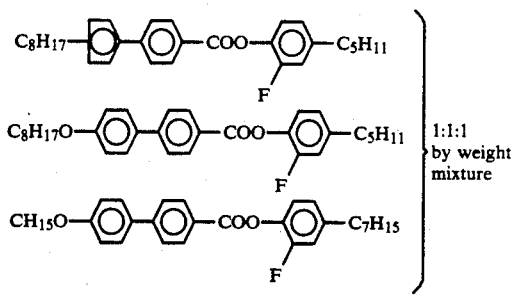

This composition had the following properties:

| (1) | Liquid crystal transitions: | | |
| --- | --- | --- | --- |
| | Sc at room temperature and below | | |
| | Sc–$S_A$ 83° C. | | |
| | $S_A$–N 109.6° C. | | |
| | N–I 137.140° C. | | |
| (2) | Ferroelectric properties: | | |
| | Temp (°C.) | Ps (nC cm$^{-2}$) | Tilt (°) |
| | 80 | 3.39 | |
| | 75 | 9.67 | 21.5 |
| | 70 | 14.11 | |
| | 65 | 17.78 | |
| | 60 | 20.67 | |
| | 55 | 23.56 | 22.0 |
| | 50 | 26.67 | |
| | 40 | 33.33 | |

EXAMPLE 4

Preparation of

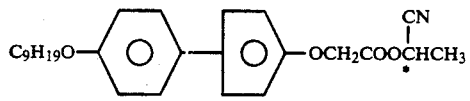

Using Routes C and E

Step C1

4-nonyloxy-4-biphenol (59.4 g), ethyl bromoacetate (26 ml), potassium carbonate (40 g) and butanone (960 ml) were stirred and heated under reflux for 28 hrs. The hot solution was filtered and allowed to cool with stirring. The product was filtered off under vacuum and dried. Yield 53.7 g: 71.6%. Hplc 99.3%.

Step C2

The product from Step C1 (53.7 g) was heated on a steam bath for 5 hrs with potassium hydroxide (20 g), water (60 ml) and 2-methoxyethanol (800 ml). About 400 ml of industrial methylated spirits was added to reduce foaming. After cooling, conc.HCL was added to adjust the mixture to pH1. The mixture was then stirred and heated for 1 hour. After cooling the solid was filtered and dried at 40° C. under vacuum. Yield 43 g.

Step E1

S-(+)-Lactic acid (200 g) was dissolved in 90% aq. methanol (2000 ml) and treated with 20%aq. potassium carbonate until the pH was 7. The solvent was removed at 50° C. under vacuum and then azeotropically removed using dichloromethane (600 ml). The lactic acid potassium salt was dissolved in dry dimethylformanide (1200 ml) and benzyl bromide (278 ml) added over 30 minutes, this solution was stirred for 16 hrs. Solvent was removed under vacuum at 40°-50° C., water (600 ml) was added and the product extracted into ether. After drying over sodium sulphate the ether layer was distilled to yield a colourless oil hp 88°-90° C. at 0.5 mmHg. Yield 279 g: 70%, glc 99.2% $[\alpha]_D^{24} = -12.9°$

Step E2

The product from Step C2 (10 g) was stirred for 16 hrs with dry toluene (120 ml), oxalyl chloride (12.4 g) and tem drops of dry dimethylformamide. The toluene was distilled off and the acid chloride redissolved in toluene (40 mls) and added to the product from Step E1 (4.41 g) on pyridine (20 mls). The mixture was stirred for 30 minutes at 20° C. then heated under reflux for 3 hours. After cooling the solution was carefully neutralised with dilute hydrochloric acid, the organic layer was removed and washed with sodium bicarbonate solution, then water. After drying, the organic layer was chromatographed on alumina. Yield 8.5 g; 65%, after crystallisation from IMS.

Step E3

The product from Step E2 (82. g) was dissolved in ethyl acetate (65 mls). 5% Pd on carbon (1 g) was added and the mixture stirred under a hydrogen armosphere overnight. The catalyst was filtered off and the solution evaporated and the white solid dried under vacuum. Yield 6.7 g; 98% mpt 150° C.

Step E4

The product from Step E3 (5 g) was stirred at 20° C. with Toluene (100 ml), dimethylformamide (10 drops) and oxalyl chloride (2.87 g) for 3 hrs. The solvents were removed and the acid chloride dissolved dry dichloromethane (100 ml). To this solution was added a mixture of dichloromethane (100 ml) and cone ammonia solution (1.5 ml) over about 10 minutes. After a further 10 minutes stirring at 20° C., water (200 mls) was added and the solution separated. The organic layer yielded 4 g of a white solid. This was dried at 40° C. under vacuum and used in the next step.

Step E5

Dimethylformamide (8 mls) was added to thionyl chloride (10.7 g), and the product from Step E4, dissolved in dimethylformamide (40 ml), was added to the cooled thionyl chloride solution. This mixture was stirred at 10°-75° C. for 2 hours and then ice/water (200 g) was added. The product was isolated by extraction into ether followed by chromatography on silica gel. After crystallisation from heptane a white solid was obtained. Yield 2.8 g, Mpt 108°-110° C.

MIXTURE EXAMPLE 4

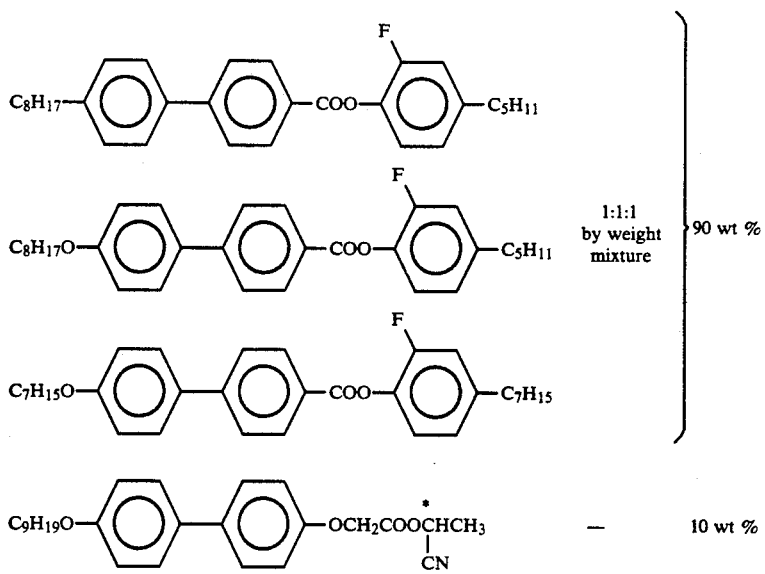

| | 1:1:1 by weight mixture | 90 wt % |
| | | 10 wt % |

This material had the following properties:

| Room temperature and below $S_C$, 91° C. $S_C$—$S_A$, 110° C. $S_A$—N, 134° C. N—I | |
|---|---|
| Temp. (°C.) | Ps (nCcm$^{-2}$) |
| 80 | 7.3 |
| 70 | 12.2 |
| 60 | 16.4 |
| 50 | 22.2 |
| 40 | 31.1 |

EXAMPLE 5

Preparation of:

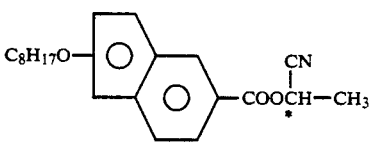

Using Route E

Step E1

S-(+)-Lactic acid (200 g) was dissolved in 90% aqueous methanol (2 L) and treated with 20% aqueous potassium carbonate until the pH was 7. The solvent was removed at 50° C. under vacuum and then azeotropically removed using dichloromethane (600 ml). The lactic acid potassium salt was dissolved in dry dimethylformanide (1200 ml) and benzyl bromide (278 ml) added over 30 minutes. This solution was stirred for 16 hours. Solvent was removed under vacuum at 40°-50° C., water (600 ml) was added and the product extracted with ether. After drying over sodium sulphate the ether layer was distilled to yield a colourless oil bp 88°-90° C. at 0.5 mm Hg. Yield 279 g, 70%, glc 99.2, $[\alpha]_0^{24} = -12.9°$.

Step E2

6-Octoxy-2-Naphthoic acid (15 g) [prepared by standard methods] was condensed with the product from Step E1 (8.33 g) by dissolving both compounds in dichloromethane (300 ml) and adding trifluoroacetic anhydride (10.7 g). The mixture was stirred at 20° C. for 3 hrs, poured into water and the organic layer washed with dilute sodium bicarbonate solution until neutral. The organic layer was dried on sodium sulphate and purified by column chromatography on alumina. After crystallisation from petroleum spirit (hp 40°-60° C.) a white solid was obtained. Yield 8.5 g; 38%.

Step E3

The product of step E2 (8.2 g) was dissolved in ethyl acetate (65 ml) 5% Pd on carbon (1 g) was added and the mixture stirred under a hydrogen atmosphere overnight. The catalyst was filtered off and the solution evaporated and the white solid product dried under vacuum. Yield 95% after recrystallisation from petroleum spirit (bp 80°-100° C.)

Step E4

The product from Step E3 (6 g) was dissolved in toluene (80 ml), oxalyl chloride (3.85 g) and dimethylformanide (6 drops) by stirring the mixture at 20° C. for 3 hrs. the excess oxalyl chloride and toluene were removed under reduced pressure and the solid was dissolved in diglyme (45 ml) and added dropwise to a stirred solution of 0.880 ammonia (50 ml). After 30 min the mixture was diluted with water (180 ml) and filtered. The solid was washed with water and dried at 40° C. under vacuum.

Yield 5.9 g; 98%.

Step E5

The product from Step E4 (5.8 g) was dissolved in dimethylformanide (20 ml) and added dropwise to a vigorously stirred solution of thionyl chloride (17.5 g) [previously redistilled] and dimethylformanide (60 ml). After 2 hrs the mexture was poured into white/ice (200 ml) and extracted with ether (2×150 ml). The combined ether extracts were washed with sodium bicarbonate, water and then dried over sodium sulphate. After remobal of solvents the product was chromatographed on silica gel and recaptallised from heptane.
Yield 3.0 g; 55%. Mp 47° C.

MIXTURE EXAMPLE 5

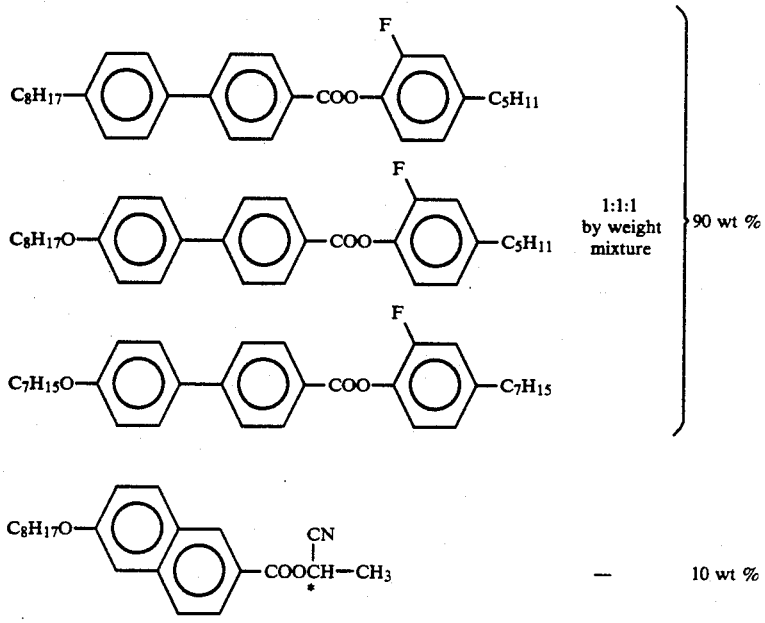

The properties of this mixture were:

| Room temp. and below $S_C$, 51.8° C. $S_C$—$S_A$, 100.7 $S_A$—N, 130.7° C. N—I | |
|---|---|
| Temp (°C.) | Ps (nC/cm$^2$) |
| 56 | 0.02 |
| 50 | 3.11 |
| 40 | 11.8 |
| 30 | 16.4 |
| 20 | 20.4 |
| 10 | 24.0 |

EXAMPLE 6

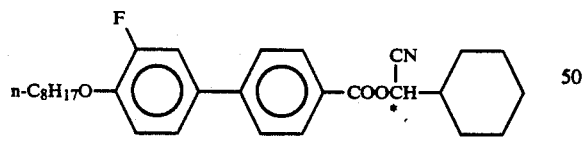

was prepared using the acid prepared in steps A11–A13 of Example 1 above, and route G. The experimental conditions for route G were the same as used for steps 3(1)–3(6) of Example 3 on pages 23–25 of WO 87/07890.

EXAMPLE 7

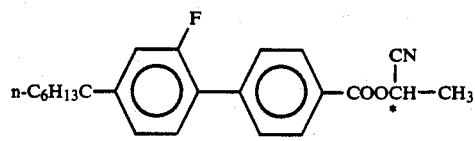

was prepared as follows:

Step A21

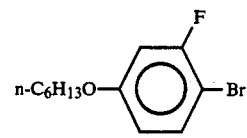

A solution of 1-bromohexane (9.33 g) in acetone (20 ml) was added dropwise to a stirred mixture of 4-bromo-3-flurophenol (9.00 g) and potassium carbonate (13.5 g) in acetone (75 ml) at room temperature. The stirred mixture was heated under reflux for 21 hr (i.e. until glc analysis revealed a complete reaction). The product was extracted into ether twice, and the combined ether extracts were washed with water, 10% sodium hydroxide, water and dried (Mg SO4). The solvent was removed under vacuo and the residue was distilled (bp 100°–105° C. at 0.1 mm Hg) to yield a colourless liquid (12.7 g, 98%).

Step A22

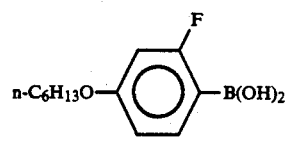

A solution of n-butyllithium (10.0M in hexane, 3.30 ml) was added dropwise to a stirred colled (−78° C.) solution of A21 (9.0 g) in dry THF (70 ml) under dry N$_2$. The stirred mixture was maintained under these conditions for 2.5 hr and then a colled solution of triisopropyl borate (11.28 g) in dry THF (50 ml) was added dropwise at −78° C. The stirred mixture was allowed to warm to room temperature overnight and then stirred for 1 hr at room temperature with 10% HCL (50 ml). The product was extracted into ether twice and the combined ethereal extracts were washed with water and dried (Mg SO₄). The solvent was removed in vacuo to afford an off-white solid (7.3 g, 99%).

Steps A23 and A24

These were performed using reaction conditions identical to those of Steps A12 and A13 of Example 1. The product was obtained as white crystals in a similar yield to that obtained in Example 1.

Using the acid produced in this way, and route E following the producedure as outlined in Example 1, the product cyanohydrin was obtained.

EXAMPLE 8

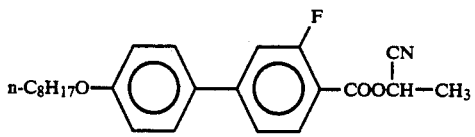

Step A31

N-Bromosuccinimide (160.4 g, 0.90 mol) was added in small portions to a stirred, cooled solution of 2-fluroaniline (100.0 g, 0.90 mol) in dry dichloromethane (400 ml). The stirred mixture was allowed to warm to 0° C. over 45 min. washed with water and dried (MgSO₄). The solvent was removed in vacuo to yield a red solid (180 g) which was steam distilled to give a colourless solid.

Step A32

Concentrated sulphuric acid (60 ml) was added dropwise to a stirred mixture of the product of Step A31 (7.50 g, 0.90 mol), water (150 ml) and glacial acetic acid (185 ml). The clear solution was cooled to −5° C. (an emulsion formed) and a solution of sodium nitrite (30.0 g, 0.44 mol) in water (100 ml) was added dropwise; the stirred mixture was maintained at −5° C. for 15 min.

A solution of potassium cyanide (128.3 g, 1.90 mol) in water (300 ml) was added dropwise to a stirred solution of copper (II) sulphate pentahydrate (118.1 g, 0.48 mol) in water (300 ml) and ice (300 g) at 10°-20° C. Sodium hydrogen carbonate (265.1 g, 3.16 mol) and cyclohexane (450 ml) were added, the temperature was raised to 50° C. and the cold diazonim salt mixture was added in portions with rapid stirring. The mixture was cooled, the organic layer was separated and the aqueous layer was washed with ether (twice). The combined organic phases were washed with water, 10% sodium hydroxide, water and dried (MgSO₄). The solvent was removed in vacuo to afford a dark brown solid (78.0 g) which was steam distilled to give an off-white solid.

Step A33

A solution of the Grignard reagent, prepared from 4-bromooctylphenyl ether (122.6 g, 0.43 mol) and magnesium (11.96 g, 0.49 mol) in dry THF (300 ml) was added dropwise to a stirred, cooled (−78° C.) solution of tri-isopropyl borate (161.7 g, 0.86 mol) in dry THF (50 ml) under dry nitrogen. The stirred mixture was allowed to warm to room temperature overnight and was then stirred at room temperature for 1 h with 10% hydrochloric acid (300 ml). The product was extracted into ether (twice), the combined ethereal extracts were washed with water and dried (MgSO₄). The solvent was removed in vacuo to yield a cream-coloured solid which was recrystallised from water to give colourless crystals.

A solution of the above (0.076 mol) in ethanol (90 ml) was added dropwise to a stirred mixture of the product of Step A32 (15.0 g, 0.069 mol) and tetrakis(triphenylphosphine)paddadium(O) (2.38 g, 2.06 mmol) in benzene (130 ml) and 2M-sodium carbonate (100 ml) at room temperature under dry nitrogen. The stirred mixture was heated under reflux (90°-95° C.) for 4.5 h (i.e., until glc analysis revealed absence of starting material). The mixture was cooled and stirred for 1 h at room temperature with 30% hydrgoen peroxide (2 ml). The mixture was further cooled to 2° C., and the product was filtered off and washed with water. The product was dried (CaCl₂) in vacuo to give fawn-coloured needles.

Step A34

The product of Step A33 was hydrolysed to the acid by conventional reflux with 50% hydrochloric acid and tol ene, until glc analysis revealed absence of the nitrile starting compound. At the end of this time the acid liquid was cooled to room temperature. The organic layer was separated and further purification was as Step A13.

The carboxylic acid product of Step A34 was made into the product via route E, using a procedure analogous to example I above.

EXAMPLE 9

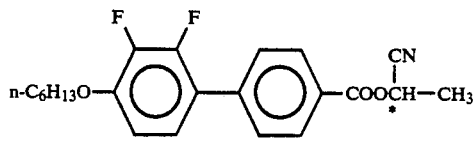

Steps A41

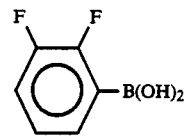

A solution of n-butyllithium (6.60 ml, 10.0M in hexane) was added dropwise to a stirred, cooled (−78° C.) solution of 1,2-difluorobenzene 97.50 g) in dry THF (70 ml) under dry N₂ The stirred mixture was maintained under these conditions for 2½ hours and then a cooled solution of tri-isopropyl borate (24.82 g) in dry THF (50 ml) was added dropwise at −78° C. The stirred mixture was allowed to warm to room temperature overnight and then stirred for 1 hour at room temperature with 10% HCl (50 ml) The product was extracted twice into ether and combined extracts were washed with water twice and dried (MgSO₄). Solvent was removed in vacuo to yield an off-white solid. yield=99%.

Step A42

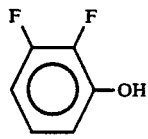

The method used was that of M. F. Hawthorne, J. Org. Chem. (1957), 22, 1001

Quantities:  A41 product          4.40 g
             10% hydrogen peroxide  30 ml Yield: 2.01 g, (80%), off-white solid, mp. 34°-36° C.

Step A43

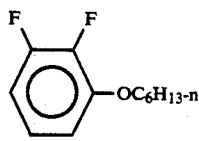

A solution of 1-bromohexane (9.33 g) in acetone (20 ml) was added dropwise to a stirred solution of A42 product (6.12 g) and potassium carbonate (13.5 g) in acetone (75 ml) at room temperature. The stirred mixture was refluxed for 21 hours (complete reaction by TLC). The product was extracted twice into ether and the combined extracts were washed with water, 10% sodium hydroxide, water, and dried (MgSO$_4$). Solvent was removed in vacuo and the residue was distilled (0.1mm Hg) to yield a colourless liquid (98%).

Step A44

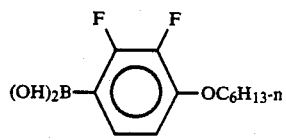

The experimental conditions for this step were the sam as step A41 above.

Steps A45 and A46

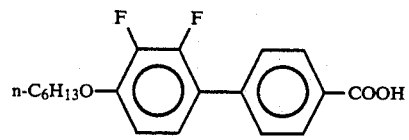

The method used was that of steps A12 and A13 described above.

Steps E1-E5

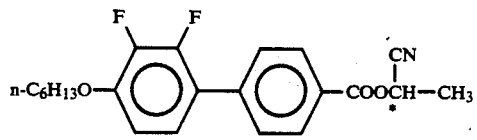

The procedure followed was analogous to that described above. By a similar procedure the n-C$_8$H$_{17}$O— analogue was prepared.

An example of the use of a compound of Formula I in a liquid crystal material and device embodying the present invention will now be described with reference to FIG. 8

Figure 8:
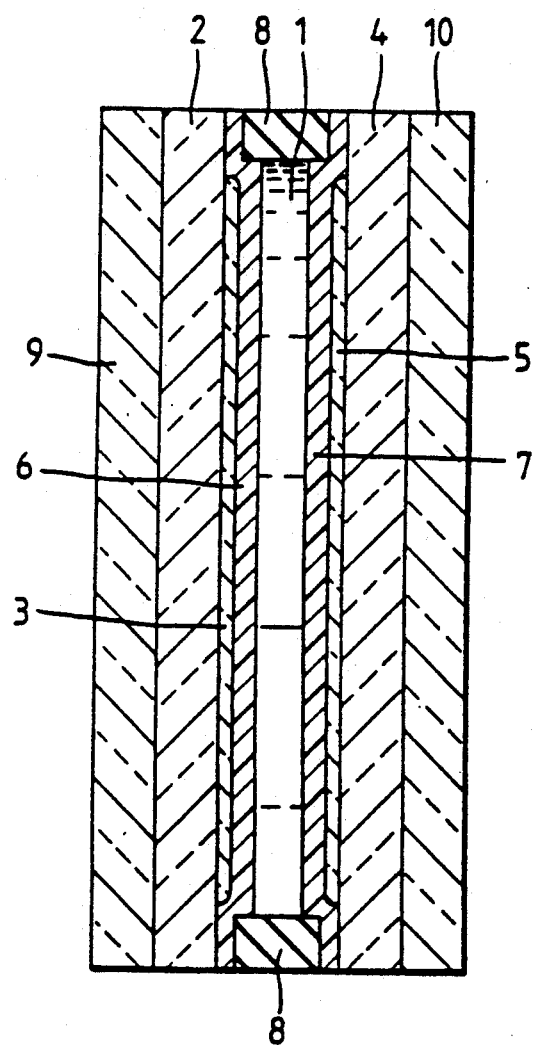

In FIG. 8 a liquid crystal cell comprises a layer 1 of liquid crystal material exhibiting a chiral smectic phase sandwiched between a glass slide 2 having a transparent conducting layer 3 on its surface, e.g. of tin oxide or indium oxide, and a glass slide 4 having a transparent conducting layer 5 on its surface. The slides 2,4 bearing the layers 3,5 are respectively coated by films 6,7 of a polyimide polymer. Prior to construction of the cell the films 6 and 7 are rubbed with a soft tissue in a given direction the rubbing directions being arranged parallel upon construction of the cell. A spacer 8 e.g. of polymethyl methacrylate, separate the slides 2, 4 to the required distance, e.g. 5 microns.

The liquid crystal material 1 is introduced between the slides 2,4 by filling the space between the slides 2, 4 and spacer 8 and sealing the spacer 8 in a vacuum in a known way. Preferably the liquid crystal material is in the smectic A, nematic or isotropic liquid phase (obtained by heating the material) when it is introduced beteen the slides 2,4 to facilitate alignment of the liquid crystal molecules with the rubbing directions on the slides 2,4.

A polarizer 9 is arranged with its polarization axis parallel to the rubbing direction on the films 6,7 and an analyzer (crossed polarizer) 10 is arranged with its polarization axis perpendicular to that rubbing direction.

When a square wave voltage (from a conventional source (not shown) varying between about +10 volts and −10 volts is applied across the cell by making contact with the layers 3 and 5 the cell is rapidly switched upon the change in sign of the voltage between a dark state and a light state as explained above.

In an alternative device (not shown) based on the cell construction shown in Figure the layers 3 and 5 may be selectively shaped in a known way, e.g. by photoetching or deposition through a mask, e.g. to provide one or more display symbols, e.g. letters, numerals, words or graphics and the like as conventionally seen on displays. The electrode portions formed thereby may be addressed in a variety of ways which include multiplexed operation.

The liquid crystal mixtures described in examples 1 to 6 above were found to be suitable for use as the layer 1.

We claim:

1. A cyanohydrin derivative of the formula I:

where R$^1$ is selected from hydrogen, C$_{1-12}$ alkyl, alkoxy, perfluoroalkyl and perfluoroalkoxy and may be straight chain or branched chain; R$^2$ is alkyl, which may be C$_{1-8}$ straight chain, C$_{1-15}$ branched chain or cyclic; r is an integer 1-10, n and m are independently 0 or 1, m+n≠0 and X is a group of the formula:

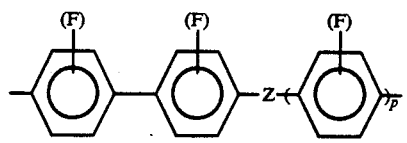

where (F) indicates that the relevant phenyl ring may carry a fluorine substituent; p is 0 or 1; and Z is a single bond where p is 0 and COO when p is 1.

2. A cyanohydrin derivative according to claim 1 having the formula:

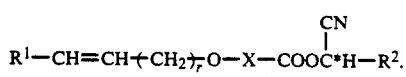

3. A cyanohydrin derivative according to claim 2 having the formula:

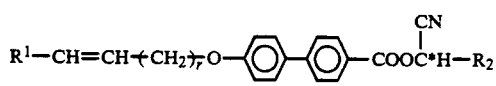

where r is 1 to 6.

4. A cyanohydrin derivative according to claim 1 having the formula:

5. A cyanohydrin derivative according to claim 4 having the formula:

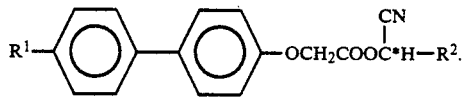

6. A cyanohydrin derivative according to claim 1 or 2 where $R^1$ is $C_3$-$C_{11}$ n-alkyl or n-alkoxy.

7. A cyanohydrin derivative according to claim 6, where $R^2$ is $C_1$-$C_5$ n-alkyl.

8. A cyanohydron derivative according to claim 7 where $R^2$ is methyl.

9. A liquid crystal material being a mixture of compounds and containing at least one cyanohydrin derivative as claimed in claim 1.

10. The liquid crystal material according to claim 9 in which the mixture additionally contains at least one compound of the formula:

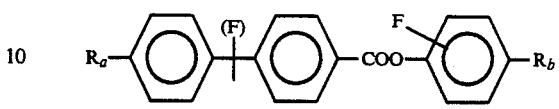

where $R_a$ and $R_b$ are independently $C_3$-$C_{12}$ alkyl or alkoxy and (F) indicates that the biphenyl system may carry a lateral fluorine substituent.

11. The liquid crystal material according to claim 9 in which the mixture additionally contains at least one compound of the formula:

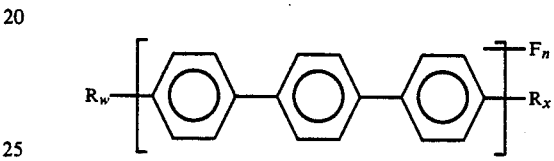

where n is 1 or 2 and $R_w$ and $R_x$ are independently $C_3$-$C_{12}$ alkyl or alkoxy.

12. The liquid crystal material according to claim 9 containing two cyanohydrin derivatives of claim 1 which have twisting effects of opposite handedness in the smectic C phase.

13. A liquid crystal electro-optic display device containing a liquid crystal material according to claim 9.

* * * * *